(12) United States Patent
Chen et al.

(10) Patent No.: US 6,232,341 B1
(45) Date of Patent: *May 15, 2001

(54) TOPICAL PHARMACEUTICAL COMPOSITIONS FOR HEALING WOUNDS

(75) Inventors: James J. T. Chen; Black J. B. Chen, both of Taipei (TW)

(73) Assignee: Hedonist Biochemical Technolog, Taipei (TW)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/166,763

(22) Filed: Oct. 5, 1998

(30) Foreign Application Priority Data

Sep. 18, 1998 (CN) .................................. 87115596

(51) Int. Cl.[7] .......................... A61K 31/29; A61K 31/60; A61K 33/24; A01N 25/00
(52) U.S. Cl. .......................... 514/503; 514/159; 514/160; 514/161; 514/162; 514/163; 424/405; 424/653
(58) Field of Search .................... 424/405, 653; 514/503, 159–163

(56) References Cited

U.S. PATENT DOCUMENTS

| | | |
|---|---|---|
| 4,001,406 | * 1/1977 | Mrozik ................................ 424/288 |
| 4,931,475 | 6/1990 | Uji . |
| 4,983,394 | 1/1991 | Hussein et al. ...................... 424/440 |
| 5,164,184 | 11/1992 | Kim .................................. 424/195.1 |
| 5,190,757 | 3/1993 | Kim .................................. 424/195.1 |
| 5,198,230 | 3/1993 | Wen . |
| 5,357,636 | * 10/1994 | Dresdner et al. ...................... 2/161.7 |
| 5,593,691 | 1/1997 | Eugster et al. ........................ 424/461 |
| 5,658,956 | * 8/1997 | Martin et al. .......................... 514/724 |
| 5,846,969 | * 12/1998 | Yoshino et al. ....................... 514/211 |

OTHER PUBLICATIONS

He, CA abstract Document No. 122: 196986, 1995.*
Zhou, CA abstract Document No. 116: 136304, 1992.*
WPI Abstract Accession No. 86–138169/22 & DE 3442120 (Von Britten), 1986.
Chemical Abstracts Accession No. 116:91435 & CN 1053187 (Liu et al), 1992.

* cited by examiner

Primary Examiner—Russell Travers
Assistant Examiner—S. Wang
(74) Attorney, Agent, or Firm—Merchant & Gould P.C.

(57) ABSTRACT

The present invention provides a topical pharmaceutical composition for wound healing, which comprises (a) borneol and (b) bismuth subgallate in effective amounts. The topical pharmaceutical composition is capable of enhancing wound healing with minor irritations to injured skin, and preventing formation of scars or granulation tissues so as to help regenerate the skin with normal tenderness and appearances.

7 Claims, 6 Drawing Sheets

TOPICAL PHARMACEUTICAL COMPOSITIONS FOR HEALING WOUNDS

FIELD OF THE INVENTION

The present invention relates to a topical pharmaceutical composition for healing wounds, especially to a topical pharmaceutical composition for enhancing healing of burns or scalds.

BACKGROUND OF THE INVENTION

Skin is the external covering of a body. It constitutes a barrier against environmental stresses. Skin is apt to suffer from injury caused by a mechanical stress (e.g., knife traumas), physical stress (e.g., sunburns or cold injury) or chemical stress (e.g., strong acids or alkalis). It is unavoidable in modem society for people to suffer skin injury (such as incised wounds, scalds or sunburns).

Skin injury caused by thermal, chemical or even electrical contact primarily results in burn wound edema and loss of intravascular fluid volume due to increased vascular permeability. Occasionally, subsequent systemic syndromes, such as hypovolemic shock or infection, may occur which are greater threats to life than the primary effects.

In spontaneous healing, dead tissue sloughs off as new epithelium begins to cover the injured area. With superficial bums (e.g., sunburns), regeneration usually occurs rapidly from uninjured epidermal elements, follicles and glands. There is non-significant or little scaring only if no infection occurs.

In the case of destruction of the epidermis or even much of the dermis, reepithelialization starts from the edges of the wound, the scattered remains of integument, or the remaining dermal appendages. This procedure is relatively slow. Excessive granulation tissue forms before being covered by epithelium. To this end, the wounds generally contract and develop to disfiguring or disabling scars unless proper and prompt treatments are employed.

The external drugs for healing wounds in humans are well known in the art. Those drugs include anti-bacterial agents, such as Povidone iodine or silver sulfadiazine; antibiotics, such as neomycin; and compound preparations with corticosteroids (e.g., hydrocortisone). However, the customary anti-bacterial agents are both irritating and toxic and are solely capable of preventing the wound from becoming infected. This expected effect of the application of antibiotics may not be achieved in view of the resistant factors prevailing in modem germs. In some cases the topical application of antibiotics (such as neomycin) may result in contact dermatitis in patients. Corticosteroids are known as the most effective anti-inflammatory agents. However, they are found to make some complications (such as some fungal infections) worse. In case of the topical application of corticosteroids with an occlusive dressing covering the treated area, miliaria, atrophic striae or bacterial infections may follow the occlusive therapy. Pituitary or cortisol suppression was found in the children subject to prolonged occlusive treatment of large areas.

Most importantly, traditional external preparations comprising the above-mentioned agent(s) are incapable to exhibit the dual functions of both promoting wound healing and preventing the formation of scars or granulation tissues. The disfiguring scars or granulation tissues usually cause secondary or even permanent adverse impacts to the patients who have recovered from traumas, especially if they are significant and visible, e.g., on the head or face.

Therefore, there is still a need in the art to develop a novel pharmaceutical composition which is both effective in enhancing wound healing and capable of preventing formation of scars or granulation tissues by helping regenerate to normal tenderness and appearance.

SUMMARY OF THE INVENTION

An object of the present invention is to provide a topical pharmaceutical composition for healing wound, which is capable of enhancing the healing of wounds with little irritation to the injured skin, and preventing formation of scars or granulation tissues by helping the injured areas to regerate to normal tenderness and appearance.

The present invention is to provide a topical pharmaceutical composition which comprises:

(a) from 0.1 to 5 percent by weight borneol; and
(b) from 3 to 15 percent by weight bismuth subgallate;
and a pharmaceutically acceptable excipient or carrier.

DETAILED DESCRIPTION OF THE INVENTION

Figure 1:
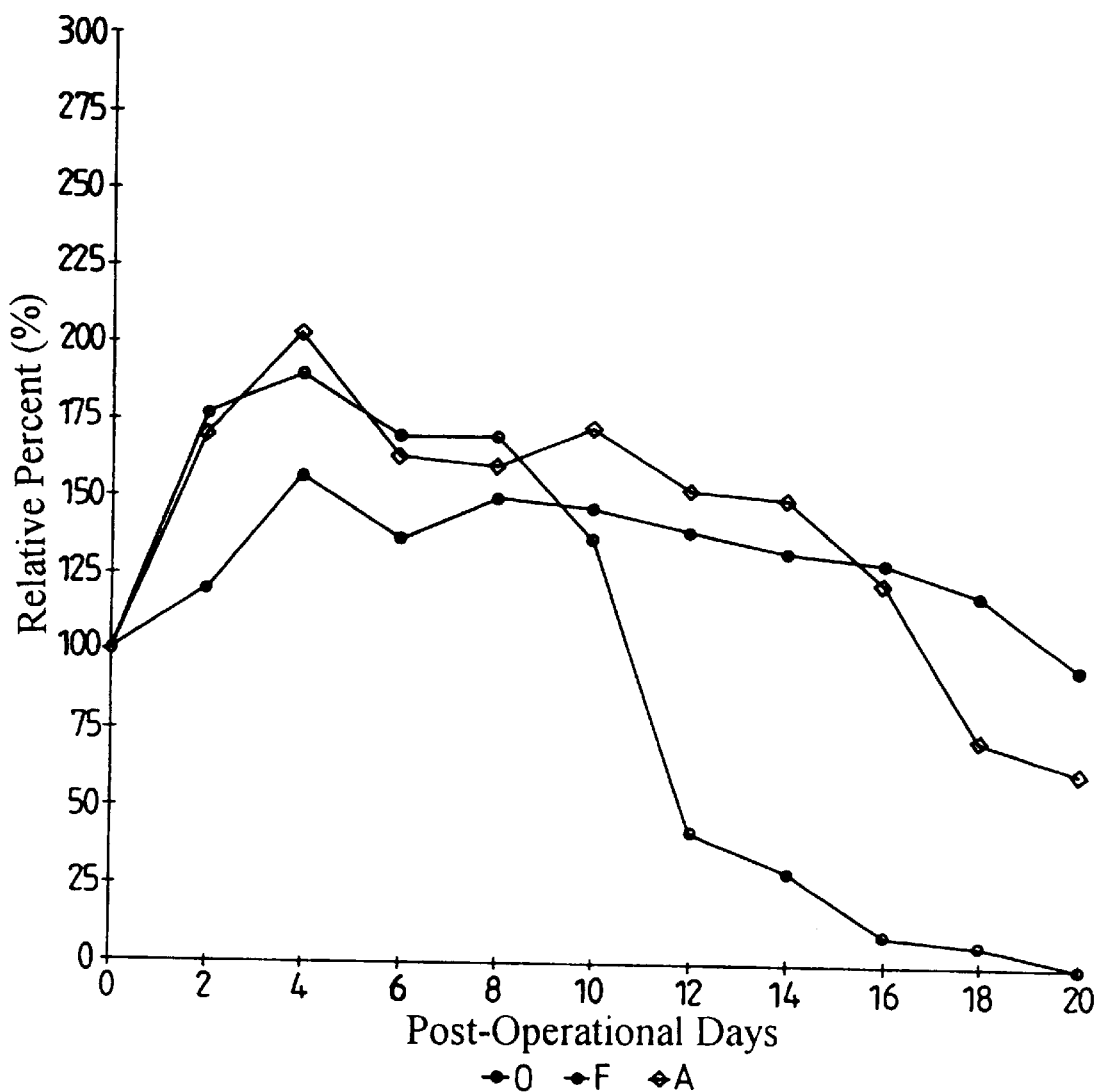
FIG. 1 shows the effect profiles on wound healing by application of a pharmaceutical composition according to the present invention on the artificial burns of rabbits compared to the excipient (Vaseline) and untreated controls, -◇-(A): Vaseline, -•-(O): untreated, -o-(F): the pharmaceutical composition according to the present invention.
Figure 2:
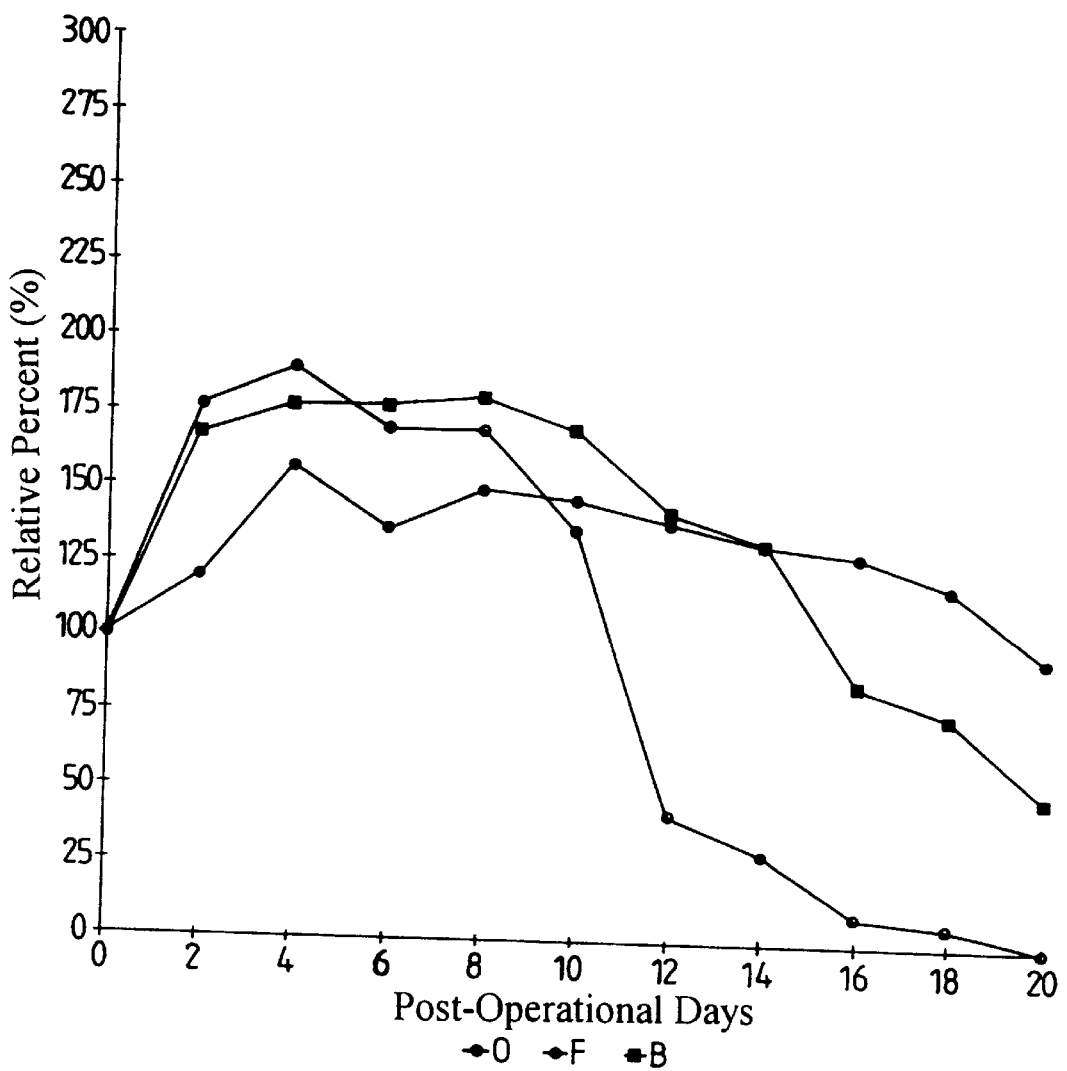
FIG. 2 shows the effect profiles on wound healing by application of a pharmaceutical composition according to the present invention on the artificial burns of rabbits compared to the single active ingredient (boric acid) and untreated controls, -■-(B): boric acid; -•-(O): untreated ; -o-(F): the pharmaceutical composition according to the present invention.

The topical pharmaceutical composition according to the present invention comprises effective amounts of borneol and bismuth subgallate, as well as a pharmaceutically acceptable excipient or carrier.

Borneol was primarily known to be isolated from *Dryobalanops aromatica* or the like and represented by the molecular formula $C_{10}H_{17}OH$. To date this compound can be synthesized in industry. Borneol has a special smell and hence has been used as a flavoring agent (e.g., see U.S. Pat. No. 4,983,394), an inactive additive in medicaments (e.g., see U.S. Pat. Nos. 5,164,184, 5,190,757 and 5,593,691). Borneol-deriving esters have been commonly utilized in perfume manufacture. U.S. Pat. 4,931,475 has proposed the use of borneol as an active agent for treating gallstones.

Bismuth subgallate is the product of the reaction among gallic acid, glacial acetic acid and bismuth nitrate which is represented by a molecular formula of $C_6H_2(OH)_3COOBi(OH)_2$. It is known as an oral anti-diarrhea agent effective in treating acute or chronic diarrhea by virtue that it can react with $H_2S$, which is present in large quantities in the intestinal tract due to abnormal fermentation, and thereby alleviate diarrhea and pains caused by gas irritation to the intestinal tract. Bismuth subgallate can also be used as a disinfectant in view of its nature as a benzene derivative.

Preferably, the topical pharmaceutical composition according to the present invention comprises:

(a) from 0.05 to 10 percent by weight borneol; and (b) from 1 to 30 percent by weight bismuth subgallate, and a pharmaceutically acceptable excipient or carrier.

More preferably, the amount of borneol in the topical pharmaceutical composition according to the present invention is from 0.1 to 5 percent by weight.

Most preferably, the amount of borneol in the topical pharmaceutical composition according to the present invention is from 0.5 to 1 percent by weight.

More preferably, the amount of bismuth subgallate in the topical pharmaceutical composition according to the present invention is from 3 to 15 percent by weight.

Most preferably, the amount of bismuth subgallate in the topical pharmaceutical composition according to the present invention is from 4 to 8 percent by weight.

The pharmaceutical composition according to the present invention may further comprise a disinfectant acceptable for medicaments, such as boric acid. In the pharmaceutical composition according to the present invention the amount of the disinfectant is preferably from 0.5 to 25 percent by weight.

The pharmaceutical composition according to the present invention may further comprise a customary anti-bacterial agent acceptable for medicaments, such as benzenesulfonamide. In the pharmaceutical composition according to the present invention the amount of the anti-bacterial agent is preferably from 0.5 to 25 percent by weight.

In an embodiment of the present invention, the pharmaceutical composition may further comprise boric acid as a disinfectant and benzenesulfonamide as an anti-bacterial agent.

Preferably, the topical pharmaceutical composition according to the present invention further comprising from 1 to 6 percent by weight boric acid and from 1 to 6 percent by weight benzenesulfonamide.

Apart from the above-mentioned active ingredients, the pharmaceutical composition according to the present invention may further comprise other traditional agents which are helpful in wound healing, such as anti-inflammatory agents, astringents, emollients or analgesics, provided that they are not detrimental to the expected efficacy. The incorporation of these traditional agents into the pharmaceutical composition according to the present invention are readily available for ordinary persons skilled in the art.

The excipients or carriers suitable for the pharmaceutical composition according to the present invention are for routine formulations in gel, paste, ointment, frost, powder, emulsion or aerosol form.

The pharmaceutical composition according to the present invention is applied without particular limitations as an external drug or in other suitable way. For instance, in a contemplation of the present invention by ordinary persons skilled in the art the pharmaceutical composition may be added to cosmetics, sun-screens or cleansing lotions for preventing or conditioning skin lesions due to exposure to the sun (ultraviolet light).

The pharmaceutical composition according to the present invention can be formulated by using traditional formulating techniques which are available to ordinary persons skilled in the art.

The following examples further illustrate the present invention, but are not intended to limit the scope of the present invention. The modifications and substitutions known to those skilled in the art are still within the scope and spirit of the present invention.

EXAMPLE 1

To prepare the pharmaceutical composition according to the present invention, the following ingredients as shown in Table 1 were blended and formulated into a paste preparation according to known formulation technology.

TABLE 1

| Ingredients | amount (mg) | percent by weight |
|---|---|---|
| borneol | 7 | 0.7% |
| bismuth subgallate | 45 | 4.5% |
| boric acid | 45 | 4.5% |
| benzenesulfonamide | 55 | 5.5% |
| vaseline | 848 | 84.8% |
| total | 1000 | 100% |

EXAMPLE 2

To prepare the controls for a comparison animal test, the following ingredients as shown in Table 2 were blended and formulated to five paste preparations (A, B, C, E and G) according to the known formulation technology.

TABLE 2

| | preparations | | | | |
|---|---|---|---|---|---|
| | A | B | C | E | G |
| boric acid | | 45 mg | | | |
| benzene-sulfonamide | | | 55 mg | | |
| borneol | | | | 7 mg | |
| bismuth subgallate | | | | | 45 mg |
| vaseline | 1000 mg | 955 mg | 945 mg | 993 mg | 955 mg |
| total | 1000 mg | 1000 mg | 1000 mg | 1000 mg | 1000 mg |

EXAMPLE 3

Animal Test

1. Method and Procedure 1.1. The Animals

Ten adult New Zealand female rabbits (average weight of 2.25 kg) were housed in well ventilated cages at room temperature in alternative 12 hour light/dark cycles and fed a regular diet (Purina Rabbit Chow, Purina Mills, Inc. Mo.).

1.2. Operation

On the operation day (day 0) four near rectangles (1.5 cm×2 cm) on the dorsal areas (two for each side) of every animal were shaved and then ironed with a 500° C. solder heater for three seconds under a general anesthesia with ketamine (35 mg/kg) and citosol (50 mg/kg) and followed by lidocaine infiltration.

1.3. Post-operation Treatments

The preparation formulated in Example 1 (designated as Treatment F), a commercial ointment for burn therapy comprising silver sulfadiazine as the main active ingredient (Flamazine, Smith & Nephew, England; designated as Treatment D), and the five preparation controls formulated in Example 2 (designated as Treatments A, B, C, E and G in accordance with their preparation nominations) were applied to any one of the wounds of five out of the ten animals where the determinations of the matches of wounds and animals were randomized. Five wounds of five out of ten animals were left untreated. The randomized arrangements of the treatments of each animal's wound are listed in Table 3. All of the wounds were covered by a sterilized (ethylene oxide) dressing (YIYONG BUZHANSHABU, Taiwan). 2 mg of drugs were applied for each wound and changed everyday. The shape of each wound was depicted in outline every other day for integrated calculations and the results were recorded. The observation ended on the 20th day after the operation.

TABLE 3

| animal No | treatments for the wounds |
| --- | --- |
| 1 | A, D, E and O |
| 2 | B, C, F and G |
| 3 | A, C, D and F |
| 4 | B, C, D and E |
| 5 | B, E, F and G |
| 6 | C, F, G and O |
| 7 | A, D, G and O |
| 8 | A, B, E and O |
| 9 | A, B, D and F |
| 10 | C, E, O and G |

2. Results 2.1 The Effects of Treatments on the Areas of Wounds

The effects of the preparation according to the present invention (Treatment F), the commercial ointment of silver sulfadiazine (Treatment D), and the five preparation controls formulated in Example 2 (Treatments A, B, C, E and G) on wound healing were assessed by measuring the wound areas of the animals in a period from the operation day to the 20th day after the operation, as shown in Table 4. Each area as measured is expressed by value ($cm^2$) of the five wounds under the same treatment.

TABLE 4

| post-operation | treatments | | | | | | | |
| --- | --- | --- | --- | --- | --- | --- | --- | --- |
|  | A | B | C | D | E | F | G | O |
|  | areas of wounds($cm^2$) | | | | | | | |
| day 0 | 3 | 3 | 3 | 3 | 3 | 3 | 3 | 3 |
| day 2 | 5.1 | 5 | 5.1 | 5 | 5.3 | 5.3 | 5.3 | 3.6 |
| day 4 | 6.1 | 5.3 | 5.7 | 5.4 | 6 | 5.7 | 5.5 | 4.7 |
| day 6 | 4.9 | 5.3 | 4.8 | 5.9 | 5.8 | 5.1 | 5.3 | 4.1 |
| day 8 | 4.8 | 5.4 | 4.6 | 5 | 5.2 | 5.1 | 5.2 | 4.5 |
| day 10 | 5.2 | 5.1 | 4.3 | 4.8 | 5.4 | 5.2 | 5.5 | 4.4 |
| day 12 | 4.6 | 4.3 | 4.1 | 4.1 | 4.5 | 1.3 | 4.8 | 4.2 |
| day 14 | 4.5 | 4 | 3.3 | 3.9 | 4.6 | 0.9 | 5.3 | 4 |
| day 16 | 3.7 | 2.6 | 2.8 | 2.4 | 3.8 | 0.3 | 4.5 | 3.9 |
| day 18 | 2.2 | 2.3 | 2.3 | 1.7 | 2.6 | 0.2 | 4 | 3.6 |
| day 20 | 1.9 | 1.5 | 2.1 | 0.9 | 2 | 0 | 3.1 | 2.9 |

The data in Table 4 are also expressed as percent changes based on the artificially injured area (1.5 cm×2 cm) as shown in Table 5.

TABLE 5

| post-operation | treatments | | | | | | | |
| --- | --- | --- | --- | --- | --- | --- | --- | --- |
|  | A | B | C | D | E | F | G | O |
|  | percent changes (%) of wound areas | | | | | | | |
| day 0 | 100 | 100 | 100 | 100 | 100 | 100 | 100 | 100 |
| day 2 | 170 | 167 | 170 | 167 | 177 | 177 | 177 | 120 |
| day 4 | 203 | 177 | 190 | 180 | 200 | 190 | 183 | 157 |
| day 6 | 163 | 177 | 160 | 197 | 193 | 170 | 177 | 137 |
| day 8 | 160 | 180 | 153 | 167 | 173 | 170 | 173 | 150 |
| day 10 | 173 | 170 | 143 | 160 | 180 | 137 | 183 | 147 |
| day 12 | 153 | 143 | 137 | 137 | 150 | 43 | 160 | 140 |
| day 14 | 150 | 133 | 110 | 130 | 153 | 30 | 177 | 133 |
| day 16 | 123 | 87 | 93 | 80 | 127 | 10 | 150 | 130 |
| day 18 | 73 | 77 | 77 | 57 | 87 | 7 | 133 | 120 |
| day 20 | 63 | 50 | 70 | 30 | 67 | 0 | 103 | 97 |

Figure 3:
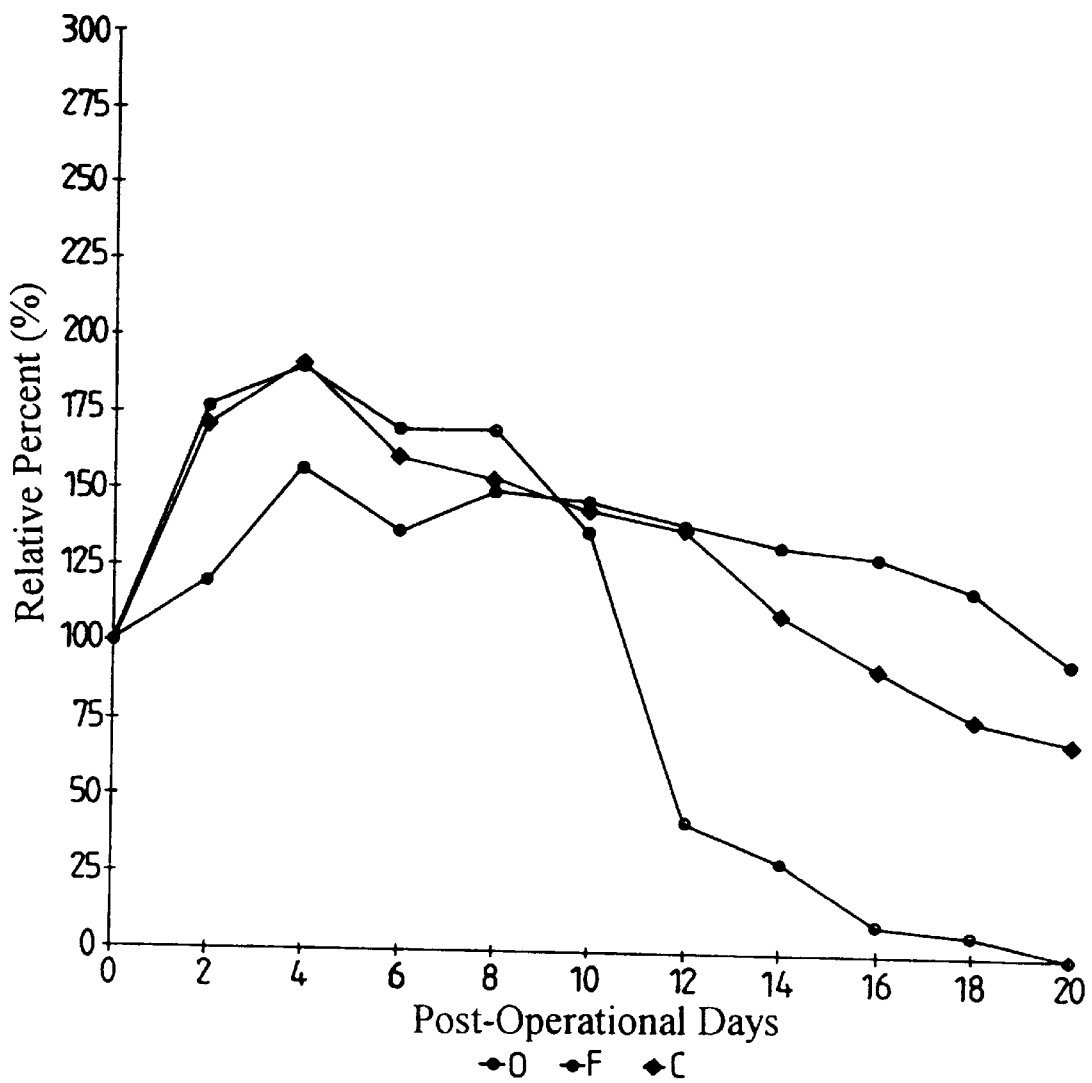
FIG. 3 shows the effect profiles on wound healing by application of a pharmaceutical composition according to the present invention on the artificial burns of rabbits compared to the single active ingredient (benzenesulfonamide) and untreated controls, -♦-(C): benzenesulfonamide; -•-(O): untreated; -o-(F): the pharmaceutical composition according to the present invention.
Figure 4:
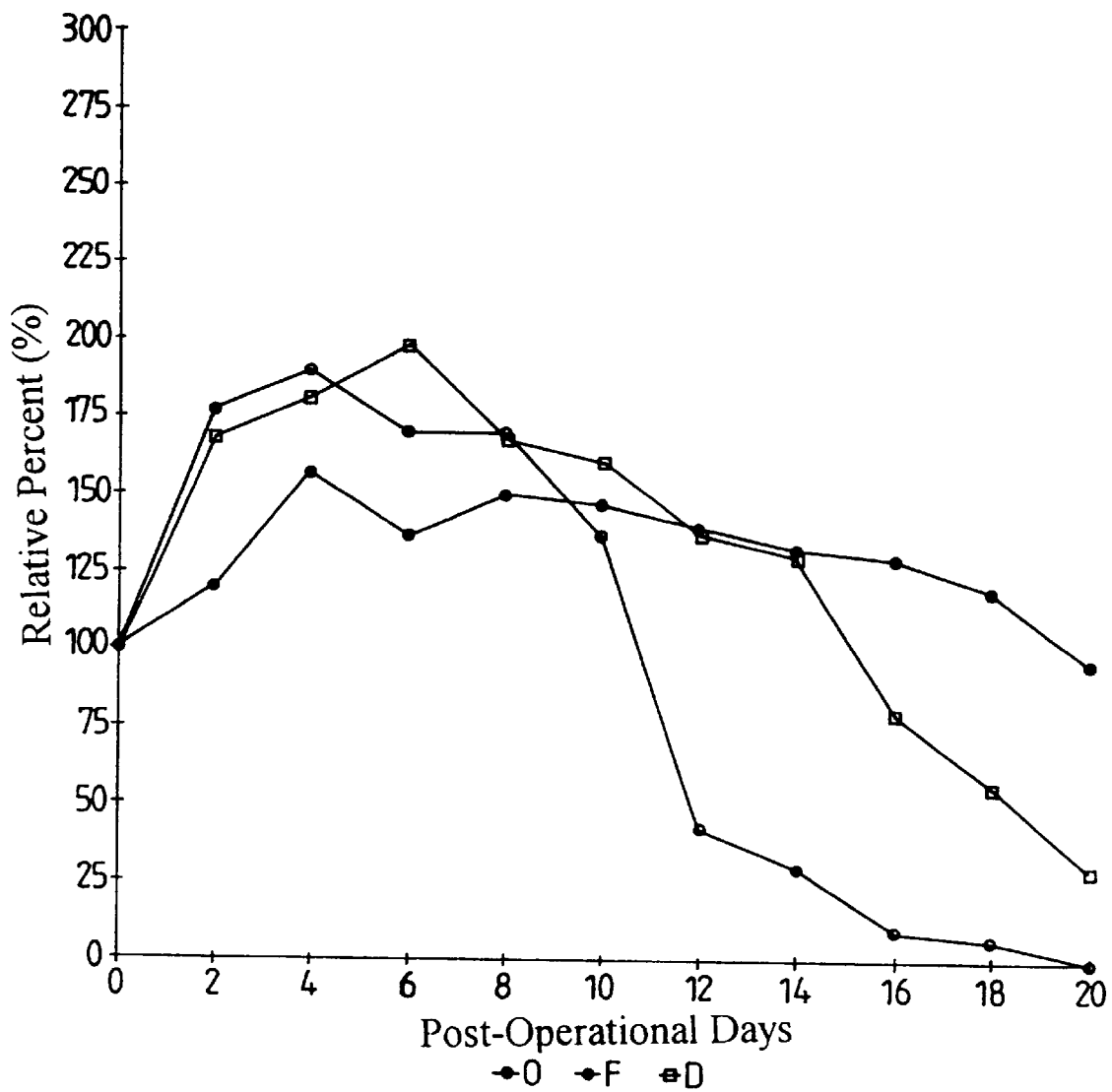
FIG. 4 shows the effect profiles on wound healing by application of a pharmaceutical composition according to the present invention on the artificial burns of rabbits compared to the single active ingredient (silver sulfadiazine) and untreated controls, -□-(D): silver sulfadiazine; -•-(O): untreated; -o-(F): the pharmaceutical composition according to the present invention.
Figure 5:
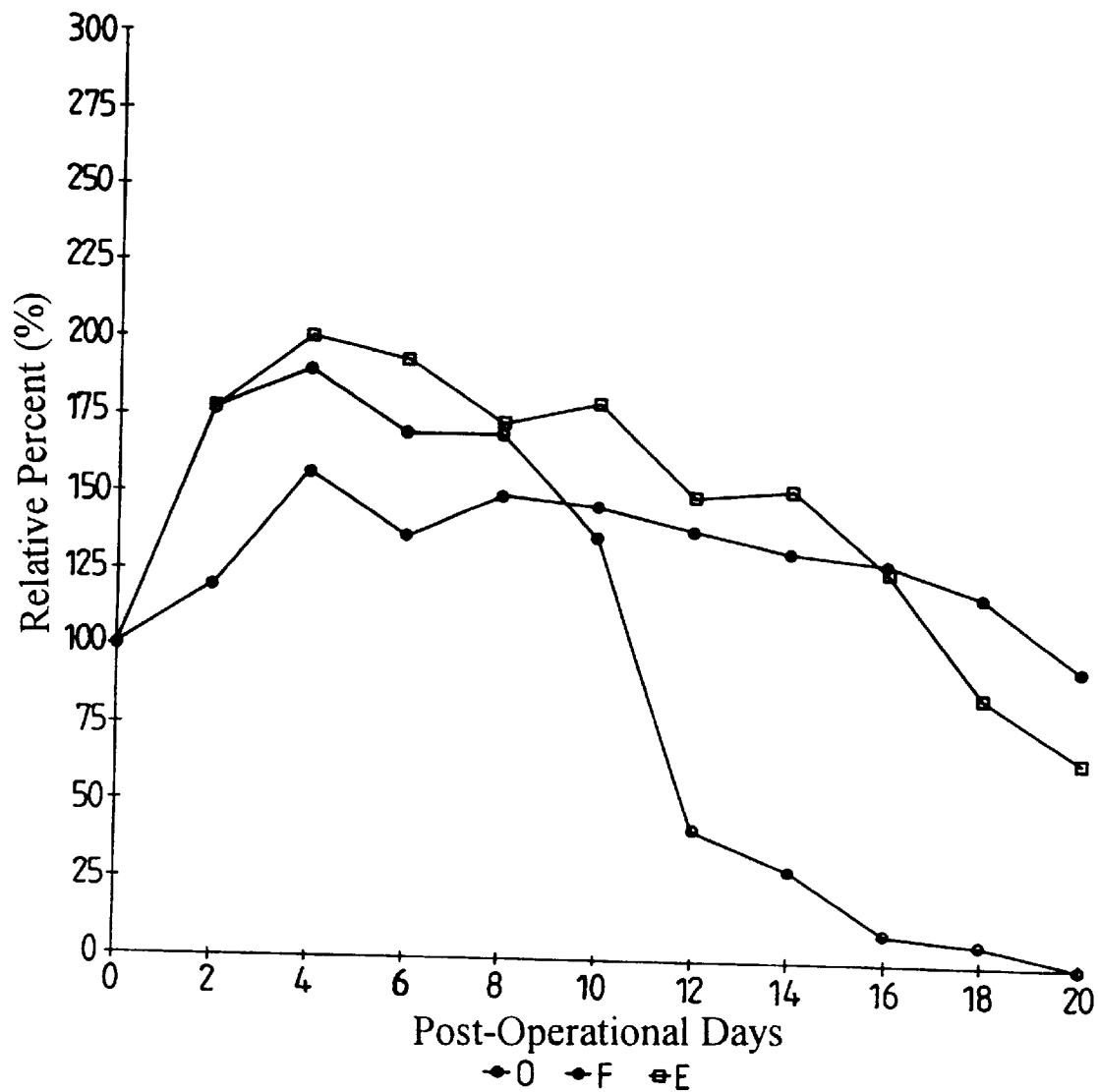
FIG. 5 shows the effect profiles on wound healing by application of a pharmaceutical composition according to the present invention on the artificial bums of rabbits compared to the single active ingredient (borneol) and untreated controls, -□-(E): borneol; -•-(O): untreated; -o-(F): the pharmaceutical composition according to the present invention.
Figure 6:
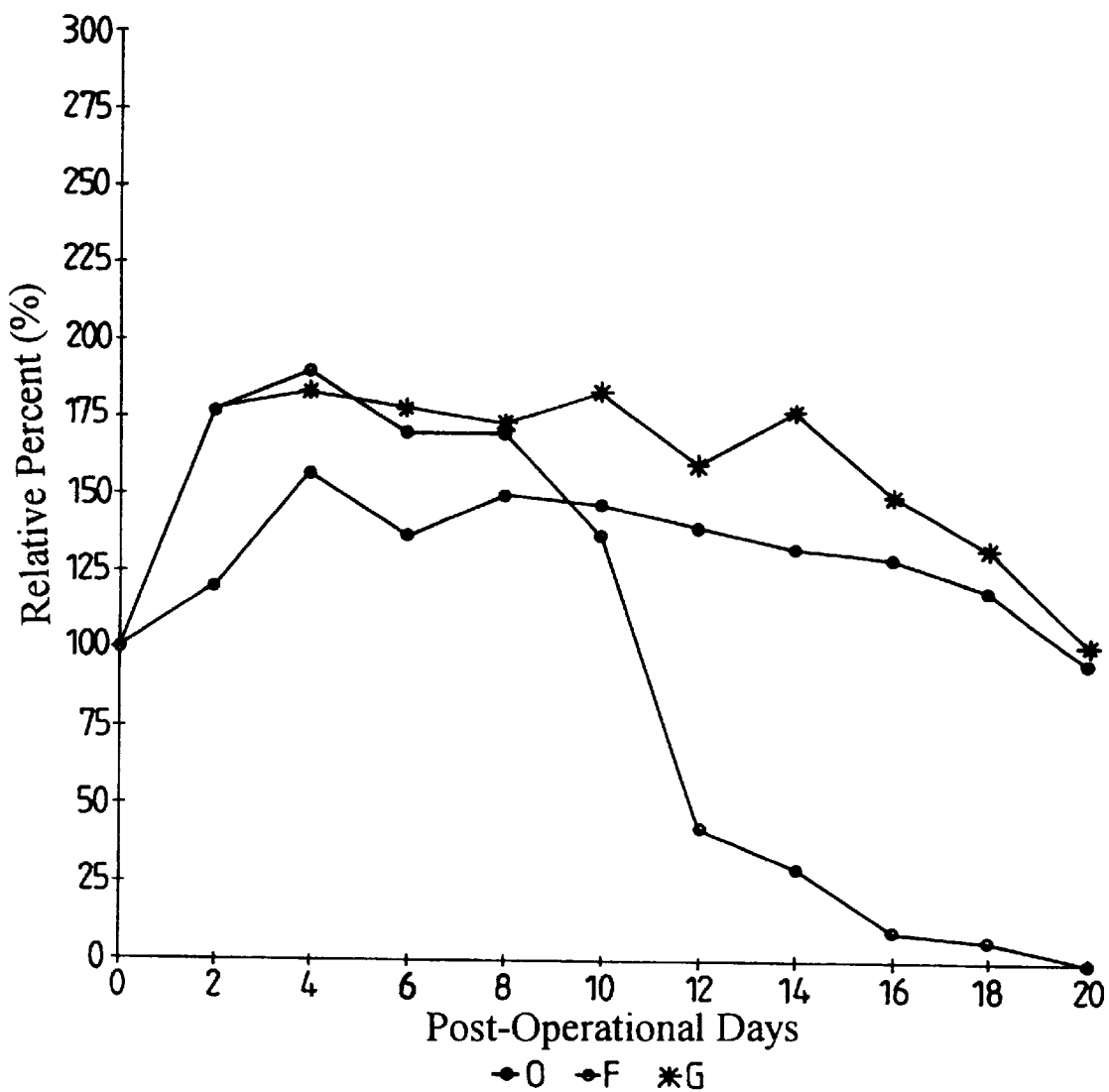
FIG. 6 shows the effect profiles on wound healing by application of a pharmaceutical composition according to the present invention on the artificial burns of rabbits compared to the single active ingredient (bismuth subgallate) and untreated controls, -*-(G): bismuth subgallate; -•-(O): untreated; -o-(F): the pharmaceutical composition according to the present invention.

To highlight the distinctive differences between the effects of the pharmaceutical composition according to the present invention and each of the controls, comparative profiles are schematically illustrated in FIGS. 1 to 6 according to the data shown in Tables 4 and 5. The wounds treated with only Vaseline (Treatment A) got better than those untreated ones and the average wound area decreased to 63%, which may contribute to the protective barrier of Vaseline covering the wounds. However, it is manifest that the wounds treated with the pharmaceutical composition according to the present invention (Treatment F) recovered completely by the 20th day after the operation. This is superior to the result of Treatment A (FIG. 1). The average wound area merely decreased by 50% (FIG. 2) when the wounds were treated with the preparation comprising boric acid as the single active ingredient (Treatment B). It is even less effective when the wounds were treated with a preparation comprising benzenesulfonamide as the single active ingredient (Treatment C) in view of the mere decrease of the average wound area by 30% (FIG. 3). Although the average area of the wounds treated with the commercial ointment (Treatment D) for the most part decreased by 70%, the tissue regeneration for the wounds treated with the pharmaceutical composition according to the present invention was accelerated at the 8th day after the operation, while the same sign was observed at the 14th day after the operation for the wounds with Treatment D (FIG. 4). The healing progress of the wounds treated with the preparation comprising borneol as the single active ingredient is similar to the ones as found in Treatments A and C (FIG. 5). As shown in FIG. 6, the wounds treated with the preparation comprising bismuth subgallate as the single active ingredient (Treatment G) appeared to be the same as those untreated ones (Treatment O).

2.2. Observations of the Tissue Regeneration

In four days after the operation, some wounds had enlarged in area as observed in every treatment. The wound areas started to decrease on the 6th day after the operation, but ulcers were also found at some scabbed wounds. On the 8th day after the operation both decreased wound areas and developing ulcers were observed in a majority of wounds, with decrustation occurring on some wounds. The wound areas decreased gradually. Decrustation occurred commonly on the 12th day after the operation. However, the decrusted wounds suffered ulcers, except for the ones with dry surfaces under Treatments D and F. In particular, the areas of the wounds under Treatment F decreased rapidly without ulcers.

On the 18th day after the operation, part of the wounds under Treatment F was recovered completely and a normal appearance was observed. Decrustation occurred at a majority of the wounds under the remaining treatments and the areas of such wounds kept decreasing, but ulcers were still ongoing with the exception of those ones with dry surfaces under Treatment D.

The wounds treated with the pharmaceutical composition according to the present invention (Treatment F) recovered entirely as observed on the 20th day after the operation. The other wounds kept decreasing in area with ulcers found at the decrusted ones, except for those wounds with dry surfaces under Treatment D.

Parts of the wounds under Treatment D also recovered by the 20th day after the operation. However, the surfaces of the regenerated tissues at the wounds under Treatment D are less smooth and have fine lines, whereas normal tenderness and appearance were observable on the surfaces of the wounds treated with the pharmaceutical composition according to the present invention (Treatment F).

In the animals testing above, formation of any granulation tissues was not found in the healing process of any of the wounds under Treatment F. Instead, slight granulation was observed during the healing process of part of the wounds under Treatment D. The formation of granulation tissues for the remaining wounds under Treatment D and all of the wounds under Treatments A, B, C, E and G was not determined since they had not yet recovered at the completion of the test.

We claim:

1. A topical pharmaceutical composition for wound healing comprising:
    (a) borneol; and
    (b) bismuth subgallate;
    and a pharmaceutically acceptable excipient or carrier, wherein the amounts of borneol and bismuth subgallate are synorgistically effective for preventing scarring and granulation.

2. The topical pharmaceutical composition according to claim 1 further comprising from 0.5 to 25 percent by weight a pharmaceutically acceptable disinfectant.

3. The topical pharmaceutical composition according to claim 2 wherein the disinfectant is boric acid.

4. The topical pharmaceutical composition according to claim 1 further comprising from 0.5 to 25 percent by weight a pharmaceutically acceptable anti-bacterial agent.

5. The topical pharmaceutical composition according to claim 4 wherein the anti-bacterial agent is benzenesulfonamide.

6. The topical pharmaceutical composition according to claim 1 further comprising from 1 to 6 percent by weight boric acid and from 1 to 6 percent by weight benzenesulfonamide.

7. The topical pharmaceutical composition according to claim 3 wherein the boric acid is present in an amount from 1 to 6 percent by weight.

* * * * *

UNITED STATES PATENT AND TRADEMARK OFFICE
CERTIFICATE OF CORRECTION

PATENT NO.   : 6,232,341 B1
DATED        : May 15, 2001
INVENTOR(S)  : Chen et al.

It is certified that error appears in the above-identified patent and that said Letters Patent is hereby corrected as shown below:

Column 3,
Line 15, "$C_6H_2(OH)_3COOBi(OH)_2$" should read -- $C_7H_5BiO_6$ --

Signed and Sealed this

Eighteenth Day of June, 2002

Attest:

Attesting Officer

JAMES E. ROGAN
Director of the United States Patent and Trademark Office